United States Patent
Allavatam et al.

(10) Patent No.: US 9,579,065 B2
(45) Date of Patent: Feb. 28, 2017

(54) CARDIAC SIGNAL VECTOR SELECTION WITH MONOPHASIC AND BIPHASIC SHAPE CONSIDERATION

(71) Applicant: Cameron Health, Inc., San Clemente, CA (US)

(72) Inventors: Venugopal Allavatam, Maple Grove, MN (US); Rick Sanghera, San Clemente, CA (US); Mark R. Schroeder, San Clemente, CA (US)

(73) Assignee: CAMERON HEALTH INC., St. Paul, MN (US)

( * ) Notice: Subject to any disclaimer, the term of this patent is extended or adjusted under 35 U.S.C. 154(b) by 256 days.

(21) Appl. No.: 14/204,478

(22) Filed: Mar. 11, 2014

(65) Prior Publication Data
US 2014/0275917 A1 Sep. 18, 2014

Related U.S. Application Data

(60) Provisional application No. 61/777,843, filed on Mar. 12, 2013.

(51) Int. Cl.
*A61B 5/0452* (2006.01)
*A61B 5/00* (2006.01)
(Continued)

(52) U.S. Cl.
CPC ........ *A61B 5/7221* (2013.01); *A61B 5/04011* (2013.01); *A61B 5/0422* (2013.01); *A61N 1/3702* (2013.01)

(58) Field of Classification Search
CPC ..... A61B 5/024; A61B 5/0402; A61B 5/0452; A61B 5/0456; A61B 5/0468;
(Continued)

(56) References Cited

U.S. PATENT DOCUMENTS 3,653,387 A 4/1972 Ceier
3,710,374 A 1/1973 Kelly
(Continued)

FOREIGN PATENT DOCUMENTS

AU 2008252063 A1 9/2011
AU 2004261227 8/2012
(Continued)

OTHER PUBLICATIONS

Bardy, Gust H, et al., "Multicenter Experience with a Pectoral Unipolar Implantable Cardioverter-Defibrillator", JACC, vol. 28, No. 2, (Aug. 1996), 400-410.
(Continued)

*Primary Examiner* — Edward Moran
*Assistant Examiner* — Michael Carey
(74) *Attorney, Agent, or Firm* — Seager, Tufte & Wickhem LLP

(57) ABSTRACT

Systems, methods and non-transient software media for performing sensing vector selection in an implantable cardiac device by assessing biphasic or monophasic characteristics of the cardiac signal in vectors under analysis. A factor associated with the biphasic or monophasic nature of the cardiac signal, as seen from a given sensing vector, can be inserted into the assessment of which of several available sensing vectors is considered "best" for purposes of cardiac signal analysis. Additional factors may be considered beyond the biphasic or monophasic nature including the quantity of turning points or inflections and amplitude variability.

19 Claims, 6 Drawing Sheets

(51) Int. Cl.
 *A61B 5/04* (2006.01)
 *A61B 5/042* (2006.01)
 *A61N 1/37* (2006.01)

(58) Field of Classification Search
 CPC . A61B 5/0472; A61B 5/7221; A61B 5/04011; A61B 5/0422; A61N 1/3702
 USPC ................ 600/510, 515, 516, 517, 518, 521
 See application file for complete search history.

(56) References Cited

U.S. PATENT DOCUMENTS

| | | |
|---|---|---|
| 3,911,925 A | 10/1975 | Tillery, Jr. |
| 4,030,509 A | 6/1977 | Heilman et al. |
| 4,157,720 A | 6/1979 | Greatbatch |
| 4,164,946 A | 8/1979 | Langer |
| 4,184,493 A | 1/1980 | Langer et al. |
| 4,191,942 A | 3/1980 | Long |
| 4,210,149 A | 7/1980 | Heilman et al. |
| RE30,387 E | 8/1980 | Denniston, III et al. |
| 4,223,678 A | 9/1980 | Langer et al. |
| 4,248,237 A | 2/1981 | Kenny |
| 4,254,775 A | 3/1981 | Langer |
| 4,291,707 A | 9/1981 | Heilman et al. |
| 4,300,567 A | 11/1981 | Kolenik et al. |
| 4,314,095 A | 2/1982 | Moore et al. |
| 4,375,817 A | 3/1983 | Engle et al. |
| 4,402,322 A | 9/1983 | Duggan |
| 4,407,288 A | 10/1983 | Langer et al. |
| 4,424,818 A | 1/1984 | Doring et al. |
| 4,450,527 A | 5/1984 | Sramek |
| 4,548,209 A | 10/1985 | Wielders et al. |
| 4,550,502 A | 11/1985 | Grayzel |
| 4,567,900 A | 2/1986 | Moore |
| 4,589,420 A | 5/1986 | Adams et al. |
| 4,595,009 A | 6/1986 | Leinders |
| 4,602,637 A | 7/1986 | Elmqvist et al. |
| 4,603,705 A | 8/1986 | Speicher et al. |
| 4,693,253 A | 9/1987 | Adams |
| 4,727,877 A | 3/1988 | Kallok |
| 4,750,494 A | 6/1988 | King |
| 4,765,341 A | 8/1988 | Mower et al. |
| 4,768,512 A | 9/1988 | Imran |
| 4,779,617 A | 10/1988 | Whigham |
| 4,800,883 A | 1/1989 | Winstrom |
| 4,830,005 A | 5/1989 | Woskow |
| 4,944,300 A | 7/1990 | Saksena |
| 4,960,126 A | 10/1990 | Conlon et al. |
| 5,044,374 A | 9/1991 | Lindemans et al. |
| 5,105,810 A | 4/1992 | Collins et al. |
| 5,105,826 A | 4/1992 | Smits et al. |
| 5,109,842 A | 5/1992 | Adinolfi |
| 5,129,392 A | 7/1992 | Bardy et al. |
| 5,133,353 A | 7/1992 | Hauser |
| 5,137,025 A | 8/1992 | Turner, II |
| 5,144,946 A | 9/1992 | Weinberg et al. |
| 5,184,616 A | 2/1993 | Weiss |
| 5,191,901 A | 3/1993 | Dahl et al. |
| 5,193,550 A | 3/1993 | Duffin |
| 5,203,348 A | 4/1993 | Dahl et al. |
| 5,215,081 A | 6/1993 | Ostroff |
| 5,230,337 A | 7/1993 | Dahl et al. |
| 5,255,692 A | 10/1993 | Neubauer et al. |
| 5,261,400 A | 11/1993 | Bardy |
| 5,271,411 A | 12/1993 | Ripley et al. |
| 5,291,895 A | 3/1994 | McIntyre |
| 5,299,119 A | 3/1994 | Kraf et al. |
| 5,300,106 A | 4/1994 | Dahl et al. |
| 5,313,953 A | 5/1994 | Yomtov et al. |
| 5,331,966 A | 7/1994 | Bennett et al. |
| 5,342,407 A | 8/1994 | Dahl et al. |
| 5,366,496 A | 11/1994 | Dahl et al. |
| 5,370,667 A | 12/1994 | Alt |
| 5,376,103 A | 12/1994 | Anderson et al. |
| 5,376,104 A | 12/1994 | Sakai et al. |
| 5,385,574 A | 1/1995 | Hauser et al. |
| 5,391,200 A | 2/1995 | KenKnight et al. |
| 5,405,363 A | 4/1995 | Kroll et al. |
| 5,411,031 A | 5/1995 | Yomtov |
| 5,411,539 A | 5/1995 | Neisz |
| 5,411,547 A | 5/1995 | Causey, III |
| 5,413,591 A | 5/1995 | Knoll |
| 5,423,326 A | 6/1995 | Wang et al. |
| 5,431,693 A | 7/1995 | Schroeppel |
| 5,439,485 A | 8/1995 | Mar et al. |
| 5,441,518 A | 8/1995 | Adams et al. |
| 5,447,521 A | 9/1995 | Anderson et al. |
| 5,464,431 A | 11/1995 | Adams et al. |
| 5,476,503 A | 12/1995 | Yang |
| 5,486,199 A | 1/1996 | Kim et al. |
| 5,501,702 A | 3/1996 | Plicchi et al. |
| 5,509,923 A | 4/1996 | Middleman et al. |
| 5,509,928 A | 4/1996 | Acken |
| 5,522,852 A | 6/1996 | White et al. |
| 5,531,765 A | 7/1996 | Pless |
| 5,531,766 A | 7/1996 | Kroll et al. |
| 5,534,019 A | 7/1996 | Paspa |
| 5,534,022 A | 7/1996 | Hoffmann et al. |
| 5,540,727 A | 7/1996 | Tockman et al. |
| 5,558,098 A | 9/1996 | Fain |
| 5,597,956 A | 1/1997 | Ito et al. |
| 5,601,607 A | 2/1997 | Adams |
| 5,603,732 A | 2/1997 | Dahl et al. |
| 5,607,455 A | 3/1997 | Armstrong |
| 5,618,287 A | 4/1997 | Fogarty et al. |
| 5,620,477 A | 4/1997 | Pless et al. |
| 5,643,328 A | 7/1997 | Cooke et al. |
| 5,645,070 A | 7/1997 | Turcott |
| 5,645,586 A | 7/1997 | Meltzer |
| 5,658,317 A | 8/1997 | Haefner et al. |
| 5,658,319 A | 8/1997 | Kroll |
| 5,658,321 A | 8/1997 | Fayram et al. |
| 5,674,260 A | 10/1997 | Weinberg |
| 5,690,648 A | 11/1997 | Fogarty et al. |
| 5,690,683 A | 11/1997 | Haefner et al. |
| 5,697,953 A | 12/1997 | Kroll et al. |
| 5,707,398 A | 1/1998 | Lu |
| 5,709,215 A | 1/1998 | Perttu et al. |
| 5,713,926 A | 2/1998 | Hauser et al. |
| 5,755,738 A | 5/1998 | Kim et al. |
| 5,766,226 A | 6/1998 | Pedersen |
| 5,776,169 A | 7/1998 | Schroeppel |
| 5,814,090 A | 9/1998 | Latterell et al. |
| 5,827,197 A | 10/1998 | Bocek et al. |
| 5,827,326 A | 10/1998 | Kroll et al. |
| 5,836,976 A | 11/1998 | Min et al. |
| 5,843,132 A | 12/1998 | Ilvento |
| 5,895,414 A | 4/1999 | Sanchez-Zambrano |
| 5,904,705 A | 5/1999 | Kroll et al. |
| 5,919,211 A | 7/1999 | Adams |
| 5,919,222 A | 7/1999 | Hjelle et al. |
| 5,925,069 A | 7/1999 | Graves et al. |
| 5,935,154 A | 8/1999 | Westlund |
| 5,941,904 A | 8/1999 | Johnston et al. |
| 5,957,956 A | 9/1999 | Kroll et al. |
| 5,987,352 A | 11/1999 | Klein et al. |
| 5,991,657 A | 11/1999 | Kim |
| 5,999,853 A | 12/1999 | Stoop et al. |
| 6,014,586 A | 1/2000 | Weinberg et al. |
| 6,016,442 A | 1/2000 | Hsu et al. |
| 6,026,325 A | 2/2000 | Weinberg et al. |
| 6,029,086 A | 2/2000 | Kim et al. |
| 6,041,251 A | 3/2000 | Kim et al. |
| 6,044,297 A | 3/2000 | Sheldon et al. |
| 6,047,210 A | 4/2000 | Kim et al. |
| 6,052,617 A | 4/2000 | Kim |
| 6,058,328 A | 5/2000 | Levine et al. |
| 6,093,173 A | 7/2000 | Balceta et al. |
| 6,095,987 A | 8/2000 | Shmulewitz et al. |
| 6,115,628 A | 9/2000 | Stadler et al. |
| H1905 H | 10/2000 | Hill |
| 6,128,531 A | 10/2000 | Campbell-smith |
| 6,144,866 A | 11/2000 | Miesel et al. |
| 6,144,879 A | 11/2000 | Gray |

(56) References Cited

U.S. PATENT DOCUMENTS

| | | |
|---|---|---|
| 6,148,230 A | 11/2000 | Kenknight |
| 6,185,450 B1 | 2/2001 | Seguine et al. |
| 6,190,324 B1 | 2/2001 | Kieval et al. |
| 6,236,882 B1 | 5/2001 | Lee et al. |
| 6,266,554 B1 | 7/2001 | Hsu et al. |
| 6,266,567 B1 | 7/2001 | Ishikawa et al. |
| 6,278,894 B1 | 8/2001 | Salo et al. |
| 6,280,462 B1 | 8/2001 | Hauser et al. |
| 6,308,095 B1 | 10/2001 | Hsu et al. |
| 6,312,388 B1 | 11/2001 | Marcovecchio et al. |
| 6,334,071 B1 | 12/2001 | Lu |
| 6,345,198 B1 | 2/2002 | Mouchawar et al. |
| 6,377,844 B1 | 4/2002 | Graen |
| 6,381,493 B1 | 4/2002 | Stadler et al. |
| 6,411,844 B1 | 6/2002 | Kroll et al. |
| 6,490,486 B1 | 12/2002 | Bradley |
| 6,493,579 B1 | 12/2002 | Gilkerson et al. |
| 6,493,584 B1 | 12/2002 | Lu |
| 6,496,715 B1 | 12/2002 | Lee et al. |
| 6,516,225 B1 | 2/2003 | Florio |
| 6,539,257 B1 | 3/2003 | KenKnight |
| 6,567,691 B1 | 5/2003 | Stadler |
| 6,574,505 B1 | 6/2003 | Warren |
| 6,587,720 B2 | 7/2003 | Hsu et al. |
| 6,625,490 B1 | 9/2003 | McClure et al. |
| 6,636,762 B2 | 10/2003 | Begemann |
| 6,647,292 B1 | 11/2003 | Bardy et al. |
| 6,658,292 B2 | 12/2003 | Kroll et al. |
| 6,658,293 B2 | 12/2003 | Vonk |
| 6,684,100 B1 | 1/2004 | Sweeney et al. |
| 6,687,540 B2 | 2/2004 | Marcovecchio |
| 6,699,200 B2 | 3/2004 | Cao et al. |
| 6,708,058 B2 | 3/2004 | Kim et al. |
| 6,708,062 B2 | 3/2004 | Ericksen et al. |
| 6,721,597 B1 | 4/2004 | Bardy et al. |
| 6,728,572 B2 | 4/2004 | Hsu et al. |
| 6,728,575 B2 | 4/2004 | Hedberg |
| 6,731,978 B2 | 5/2004 | Olson et al. |
| 6,738,667 B2 | 5/2004 | Deno et al. |
| 6,745,076 B2 | 6/2004 | Wohlgemuth et al. |
| 6,751,502 B2 | 6/2004 | Daum et al. |
| 6,754,528 B2 | 6/2004 | Bardy et al. |
| 6,760,615 B2 | 7/2004 | Ferek-Petric |
| 6,766,190 B2 | 7/2004 | Ferek-Petric |
| 6,778,860 B2 | 8/2004 | Ostroff et al. |
| 6,788,974 B2 | 9/2004 | Bardy et al. |
| 6,810,284 B1 | 10/2004 | Bradley |
| 6,834,204 B2 | 12/2004 | Ostroff et al. |
| 6,856,835 B2 | 2/2005 | Bardy et al. |
| 6,865,417 B2 | 3/2005 | Rissmann et al. |
| 6,866,044 B2 | 3/2005 | Bardy et al. |
| 6,889,079 B2 | 5/2005 | Bocek et al. |
| 6,892,092 B2 | 5/2005 | Palreddy et al. |
| 6,909,916 B2 | 6/2005 | Spinelli et al. |
| 6,927,721 B2 | 8/2005 | Ostroff |
| 6,937,907 B2 | 8/2005 | Bardy et al. |
| 6,950,705 B2 | 9/2005 | Bardy et al. |
| 6,952,608 B2 | 10/2005 | Ostroff |
| 6,952,610 B2 | 10/2005 | Ostroff et al. |
| 6,954,670 B2 | 10/2005 | Ostroff |
| 6,959,212 B2 | 10/2005 | Hsu et al. |
| 6,975,904 B1 | 12/2005 | Sloman |
| 6,980,856 B2 | 12/2005 | Sullivan et al. |
| 6,988,003 B2 | 1/2006 | Bardy et al. |
| 6,993,379 B1 | 1/2006 | Kroll et al. |
| 6,996,434 B2 | 2/2006 | Marcovecchio et al. |
| 7,016,730 B2 | 3/2006 | Ternes |
| 7,020,523 B1 | 3/2006 | Lu et al. |
| 7,027,858 B2 | 4/2006 | Cao et al. |
| 7,027,862 B2 | 4/2006 | Dahl et al. |
| 7,031,764 B2 | 4/2006 | Schwartz et al. |
| 7,039,459 B2 | 5/2006 | Bardy et al. |
| 7,039,463 B2 | 5/2006 | Marcovecchio |
| 7,039,465 B2 | 5/2006 | Bardy et al. |
| 7,043,299 B2 | 5/2006 | Erlinger et al. |
| 7,062,329 B2 | 6/2006 | Ostroff et al. |
| 7,065,407 B2 | 6/2006 | Bardy et al. |
| 7,065,410 B2 | 6/2006 | Bardy et al. |
| 7,069,080 B2 | 6/2006 | Bardy et al. |
| 7,076,294 B2 | 7/2006 | Bardy et al. |
| 7,076,296 B2 | 7/2006 | Bardy et al. |
| 7,085,599 B2 | 8/2006 | Kim et al. |
| 7,090,682 B2 | 8/2006 | Sanders et al. |
| 7,092,754 B2 | 8/2006 | Bardy et al. |
| 7,120,495 B2 | 10/2006 | Bardy et al. |
| 7,120,496 B2 | 10/2006 | Bardy et al. |
| 7,130,689 B1 | 10/2006 | Turcott |
| 7,146,212 B2 | 12/2006 | Bardy et al. |
| 7,149,575 B2 | 12/2006 | Ostroff et al. |
| 7,162,301 B2 | 1/2007 | Kim et al. |
| 7,167,747 B2 | 1/2007 | Gunderson et al. |
| 7,177,689 B2 | 2/2007 | Ternes et al. |
| 7,181,274 B2 | 2/2007 | Rissmann et al. |
| 7,181,281 B1 | 2/2007 | Kroll |
| 7,184,818 B2 | 2/2007 | Kim et al. |
| 7,191,004 B2 | 3/2007 | Kim et al. |
| 7,194,302 B2 | 3/2007 | Bardy et al. |
| 7,248,921 B2 | 7/2007 | Palreddy et al. |
| 7,266,409 B2 | 9/2007 | Gunderson |
| 7,330,757 B2 | 2/2008 | Ostroff et al. |
| 7,366,569 B2 | 4/2008 | Belalcazar |
| 7,379,772 B2 | 5/2008 | Bardy et al. |
| 7,392,085 B2 | 6/2008 | Warren et al. |
| 7,412,287 B2 | 8/2008 | Yonce et al. |
| 7,623,909 B2 | 11/2009 | Sanghera et al. |
| 7,627,367 B2 | 12/2009 | Warren et al. |
| 7,783,340 B2 | 8/2010 | Sanghera et al. |
| 8,200,341 B2 | 6/2012 | Sanghera et al. |
| 8,483,843 B2 | 7/2013 | Sanghera et al. |
| 8,565,878 B2 | 10/2013 | Allavatam et al. |
| 2001/0027330 A1 | 10/2001 | Sullivan et al. |
| 2001/0034487 A1 | 10/2001 | Cao et al. |
| 2002/0035377 A1 | 3/2002 | Bardy et al. |
| 2002/0035378 A1 | 3/2002 | Bardy et al. |
| 2002/0035379 A1 | 3/2002 | Bardy et al. |
| 2002/0035381 A1 | 3/2002 | Bardy et al. |
| 2002/0095184 A1 | 7/2002 | Bardy et al. |
| 2002/0107544 A1 | 8/2002 | Ostroff et al. |
| 2002/0107545 A1 | 8/2002 | Rissmann et al. |
| 2002/0165587 A1 | 11/2002 | Zhang et al. |
| 2002/0169484 A1 | 11/2002 | Mathis et al. |
| 2003/0083710 A1 | 5/2003 | Ternes et al. |
| 2003/0088277 A1 | 5/2003 | Ostroff |
| 2003/0144700 A1 | 7/2003 | Brown et al. |
| 2003/0191500 A1 | 10/2003 | Stokes et al. |
| 2003/0204215 A1 | 10/2003 | Gunderson et al. |
| 2004/0064162 A1 | 4/2004 | Manrodt et al. |
| 2004/0088018 A1 | 5/2004 | Sawchuk |
| 2004/0215240 A1 | 10/2004 | Lovett et al. |
| 2004/0230229 A1 | 11/2004 | Lovett et al. |
| 2004/0230243 A1 | 11/2004 | Haefner et al. |
| 2004/0230249 A1 | 11/2004 | Haefner |
| 2004/0236379 A1 | 11/2004 | Bardy et al. |
| 2004/0254611 A1 | 12/2004 | Palreddy et al. |
| 2004/0254613 A1 | 12/2004 | Ostroff et al. |
| 2005/0004613 A1 | 1/2005 | Zhang et al. |
| 2005/0004615 A1 | 1/2005 | Sanders |
| 2005/0049644 A1 | 3/2005 | Warren et al. |
| 2005/0192505 A1 | 9/2005 | Ostroff et al. |
| 2005/0192507 A1 | 9/2005 | Warren et al. |
| 2005/0203581 A1 | 9/2005 | Spinelli et al. |
| 2005/0245976 A1 | 11/2005 | Wang |
| 2006/0036288 A1 | 2/2006 | Bocek et al. |
| 2006/0052830 A1 | 3/2006 | Spinelli et al. |
| 2006/0079796 A1 | 4/2006 | Marcovecchio et al. |
| 2006/0085038 A1 | 4/2006 | Linder et al. |
| 2006/0116595 A1 | 6/2006 | Palreddy et al. |
| 2006/0116730 A1 | 6/2006 | Gunderson |
| 2006/0122676 A1 | 6/2006 | Ko et al. |
| 2006/0161205 A1 | 7/2006 | Mitrani et al. |
| 2006/0167502 A1 | 7/2006 | Haefner |
| 2006/0173498 A1 | 8/2006 | Banville et al. |
| 2006/0235476 A1 | 10/2006 | Gunderson et al. |
| 2006/0241512 A1 | 10/2006 | Kwok et al. |

(56) References Cited

U.S. PATENT DOCUMENTS

| | | | |
|---|---|---|---|
| 2006/0247694 A1* | 11/2006 | Dong | A61N 1/3712 607/9 |
| 2007/0123947 A1 | 5/2007 | Wenger et al. | |
| 2007/0232944 A1 | 10/2007 | Ghanem et al. | |
| 2007/0232945 A1 | 10/2007 | Kleckner et al. | |
| 2007/0232948 A1 | 10/2007 | Stadler et al. | |
| 2007/0233196 A1 | 10/2007 | Stadler et al. | |
| 2007/0233198 A1 | 10/2007 | Ghanem et al. | |
| 2007/0239044 A1 | 10/2007 | Ghanem et al. | |
| 2007/0239045 A1 | 10/2007 | Ghanem et al. | |
| 2007/0239046 A1 | 10/2007 | Ghanem et al. | |
| 2007/0239047 A1 | 10/2007 | Ghanem et al. | |
| 2007/0239048 A1 | 10/2007 | Ghanem et al. | |
| 2007/0239049 A1 | 10/2007 | Ghanem et al. | |
| 2007/0239050 A1 | 10/2007 | Ghanem et al. | |
| 2007/0239051 A1 | 10/2007 | Ghanem et al. | |
| 2007/0239220 A1 | 10/2007 | Greenhut et al. | |
| 2007/0270704 A1 | 11/2007 | Ghanem et al. | |
| 2007/0276445 A1 | 11/2007 | Sanghera et al. | |
| 2007/0276447 A1 | 11/2007 | Sanghera et al. | |
| 2007/0276452 A1 | 11/2007 | Sanghera et al. | |
| 2008/0188901 A1 | 8/2008 | Sanghera et al. | |
| 2008/0243025 A1 | 10/2008 | Holmstrom et al. | |
| 2008/0269813 A1* | 10/2008 | Greenhut | A61B 5/042 607/5 |
| 2008/0275521 A1 | 11/2008 | Warren et al. | |
| 2009/0093731 A1 | 4/2009 | Palreddy et al. | |
| 2012/0245651 A1 | 9/2012 | Sanghera et al. | |
| 2013/0274822 A1 | 10/2013 | Sanghera et al. | |

FOREIGN PATENT DOCUMENTS

| | | |
|---|---|---|
| DE | 29801807 U1 | 6/1998 |
| EP | 0095727 A1 | 12/1983 |
| EP | 0316616 A2 | 5/1989 |
| EP | 0316616 A3 | 5/1989 |
| EP | 0347353 A1 | 12/1989 |
| EP | 0517494 A2 | 12/1992 |
| EP | 0517494 B1 | 12/1992 |
| EP | 0518599 A2 | 12/1992 |
| EP | 0518599 B1 | 12/1992 |
| EP | 0536873 B1 | 12/1992 |
| EP | 0517494 A3 | 3/1993 |
| EP | 0536873 A1 | 4/1993 |
| EP | 0586858 A1 | 3/1994 |
| EP | 0586858 B1 | 3/1994 |
| EP | 0627237 A1 | 12/1994 |
| EP | 0641573 A2 | 3/1995 |
| EP | 0641573 A3 | 3/1995 |
| EP | 0677301 A1 | 10/1995 |
| EP | 0813889 A2 | 12/1997 |
| EP | 0917887 A1 | 5/1999 |
| EP | 0923130 A1 | 6/1999 |
| EP | 1000634 A1 | 5/2000 |
| EP | 1184050 A2 | 3/2002 |
| EP | 1745741 A1 | 1/2007 |
| WO | WO-9319809 A1 | 10/1993 |
| WO | WO-9729802 A2 | 8/1997 |
| WO | WO-9825349 A1 | 6/1998 |
| WO | WO-9903534 A1 | 1/1999 |
| WO | WO-9937362 A1 | 7/1999 |
| WO | WO-9948554 A1 | 9/1999 |
| WO | WO-9953991 A1 | 10/1999 |
| WO | WO-0222208 A3 | 3/2000 |
| WO | WO-0041766 A1 | 7/2000 |
| WO | WO-0050120 A1 | 8/2000 |
| WO | WO-0143649 A1 | 6/2001 |
| WO | WO-0156166 A2 | 8/2001 |
| WO | WO-0222208 A2 | 3/2002 |
| WO | WO-0224275 A2 | 3/2002 |
| WO | WO-0224275 A3 | 5/2002 |
| WO | WO-02068046 A1 | 9/2002 |
| WO | WO-03018121 A2 | 3/2003 |
| WO | WO-03020367 A1 | 3/2003 |
| WO | WO-03065613 A1 | 8/2003 |
| WO | WO-2004091720 A2 | 10/2004 |
| WO | WO-2004105871 A1 | 12/2004 |
| WO | WO-2004108212 A2 | 12/2004 |
| WO | WO-2007089959 A1 | 8/2007 |
| WO | WO-2007140207 A1 | 12/2007 |
| WO | WO-2007140209 A2 | 12/2007 |
| WO | WO-2007140209 A3 | 12/2007 |
| WO | WO-2007140214 A1 | 12/2007 |

OTHER PUBLICATIONS

Burri, et al., "Utility of the Surface ECG Before VDD Pacemaker Implantation", International Journal of Cardiology, vol. 117, No. 2, (Apr. 25, 2007), 211-213.

Chrysostomakis, et al., "Implantable Loop Recorder Undersensing Mimicking Complete Heart Block", Europace; vol. 4, No. 2, (2002), 211-213.

Chrysostomakis, et al., "Sensing Issues Related to the Clinical Use of Implantable Loop Recorders", Europace; vol. 5, No. 2, (2003), 143-148.

Friedman, Richard A, et al., "Implantable Defibrillators in Children: From Whence to Shock", Journal of Cardiovascular Electrophysiology, vol. 12, No. 3, (Mar. 2001), 361-362.

Ge, Dingfei, et al., "Cardiac Arrhythmia Classification Using Autoregressive Modeling", BioMedical Engineering OnLine, [Online]. Retrieved from the Internet: <http://www.biomedical-engineering-online.com>, (Nov. 13, 2002), 12 pgs.

Gradaus, Rainer, et al., "Nonthoracotomy Implantable Cardioverter Defibrillator Placement in Children: Use of Subcutaneous Array Leads and Abdominally Placed Implantable Cardioverter Defibrillators in Children", Journal of Cardiovascular Electrophysiology, 12(3), (Mar. 2001), 356-360.

Higgins, Steven L, et al., "The First Year Experience with the Dual Chamber ICD", Pace, vol. 23, (Jan. 18-25, 2000).

Mirowski, M, et al., "Automatic Detection and Defibrillation of Lethal Arrhythmias—A New Concept", JAMA, vol. 213, No. 4, (Jul. 27, 1970), 615-616.

Olson, Walter H, et al., "Onset and Stability for Ventricular Tachyarrhythmia Detection in an Implantable Pacer-Cardioverter-Defibrillator", IEEE, (1987), 167-170.

Schuder, John C, "Completely Implanted Defibrillator", JAMA, vol. 214, No. 6, (Nov. 9, 1970), 1123 pg.

Schuder, John C, et al., "Experimental Ventricular Defibrillation with an Automatic and Completely Implanted System", Trans. Am. Soc. Artif. Int. Organs, vol. 16, (1970), 207-212.

Schuder, John C, et al., "Standby Implanted Defibrillators", Arch Intern. Med, vol. 127, (Feb. 1971), 317 pg.

Schuder, John C, "The Role of an Engineering Oriented Medical Research Group in Developing Improved Methods & Devices for Achieving Ventricular Defibrillation: The University of Missouri Experience", PACE, vol. 16, Part I, (Jan. 1993), 95-124.

Schuder, John C, et al., "Transthoracic Ventricular Defibrillation in the Dog with Truncated and Untruncated Exponential Stimuli", IEEE Trans. on Bio-Medical Engin., vol. BME-18, No. 6, (Nov. 1971), 410-415.

Schwake, H., et al., "Komplikationen mit Sonden bei 340 Patienten mit einem implantierbaren Kardioverter/Defibrilator", Z Kardiol, vol. 88, No. 8, (1999), 559-565.

Throne, Robert D, et al., "A Comparison of Four New Time-Domain Techniques for Discriminating Monomorphic Ventricular Tachycardia from Sinus Rhythm Using Ventricular Waveform Morphology", IEEE Transactions on Biomedical Engineering, vol. 38, No. 6, (Jun. 1991), 561-570.

Tietze, U, et al., "Halbleiter-Schaltungstechnik", © Springer-Verlag (Berlin, Germany), (1991), 784-786.

Valenzuela, Terrence D, et al., "Outcomes of Rapid Defibrillation by Security Officers After Cardiac Arrest in Casinos", The New England Journal of Medicine, vol. 343, No. 17, (Oct. 26, 2000), 1206-1209.

(56) References Cited

OTHER PUBLICATIONS

Walters, R A, et al., "Analog to Digital Conversion Techniques in Implantable Devices", Annual International Conference of the IEEE Engineering in Medicine and Biology Society, vol. 13, No. 4, (1991), 1674-1676.

* cited by examiner

CARDIAC SIGNAL VECTOR SELECTION WITH MONOPHASIC AND BIPHASIC SHAPE CONSIDERATION

CROSS REFERENCE TO RELATED APPLICATIONS

The present application claims the benefit of and priority to U.S. Provisional Patent Application No. 61/777,843, filed Mar. 12, 2013, the disclosure of which is incorporated herein by reference.

BACKGROUND

Active implantable cardiac devices include such systems as cardiac monitors, pacemakers, implantable defibrillators and cardiac resynchronization devices, among others. Such systems typically include implantable electrodes coupled to circuitry for sensing and analyzing electrical signals. Some systems are designed with multiple sensing electrodes to define multiple sensing vectors. For example, implantable transvenous and subcutaneous systems for monitoring and treating cardiac conditions are disclosed in U.S. Pat. No. 7,623,909, titled IMPLANTABLE MEDICAL DEVICES AND PROGRAMMERS ADAPTED FOR SENSING VECTOR SELECTION, the disclosure of which is incorporated herein by reference. The '909 patent discusses methods for selecting a default or primary sensing vector from among several available sensing vectors. Some examples allow for selection of primary and secondary vectors in the '909 patent.

Additional examples of implantable systems with multiple sensing vectors can be found in U.S. Pat. No. 8,200,341, titled SENSING VECTOR SELECTION IN A CARDIAC STIMULUS DEVICE WITH POSTURAL ASSESSMENT, U.S. Pat. No. 7,392,085, titled MULTIPLE ELECTRODE VECTORS FOR IMPLANTABLE CARDIAC TREATMENT DEVICES, and U.S. Pat. No. 5,331,966, titled SUBCUTANEOUS MULTI-ELECTRODE SENSING SYSTEM, METHOD AND PACER, the disclosures of which are incorporated herein by reference. Continuing enhancement of such systems is desired.

OVERVIEW

In illustrative examples, the present invention provides systems, methods and software apparatuses for performing sensing vector selection in an implantable cardiac device by assessing biphasic or monophasic characteristics of the cardiac signal in vectors under analysis. A factor associated with the biphasic or monophasic nature of the cardiac signal, as seen from a given sensing vector, can be inserted into the assessment of which of several available sensing vectors is considered "best" for purposes of cardiac signal analysis. Other variables may also be considered.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Each of the following non-limiting examples can stand on its own, or can be combined in various permutations or combinations with one or more of the other examples.

As used herein, a signal is sensed by an implantable cardiac device system, events are detected in the sensed signal, and cardiac rhythms are classified by use of the detected events. Detected events may also be referred to as detections. Classification of the cardiac rhythms may be referred to as rhythm analysis. Cardiac rhythm classification can include identification of malignant conditions, such as ventricular fibrillation or certain tachyarrhythmias, for example.

The present invention may be used in implantable monitoring or therapy systems. Implantable therapy systems make therapy/stimulus decisions in reliance upon rhythm classification, while monitoring systems make data recording decisions using rhythm classification, where applicable. Therapy systems may deliver electrical, pharmaceutical or other therapy. Some illustrative implementations of the present invention may be in pacemakers and defibrillators, though other implementations are also envisioned. Any of these systems can, if so configured and enabled, generate annunciating (audible tones or palpable vibrations) or communicating (telemetry) signals in response to rhythm classification, in addition to or as an alternative to therapy.

Figure 1:
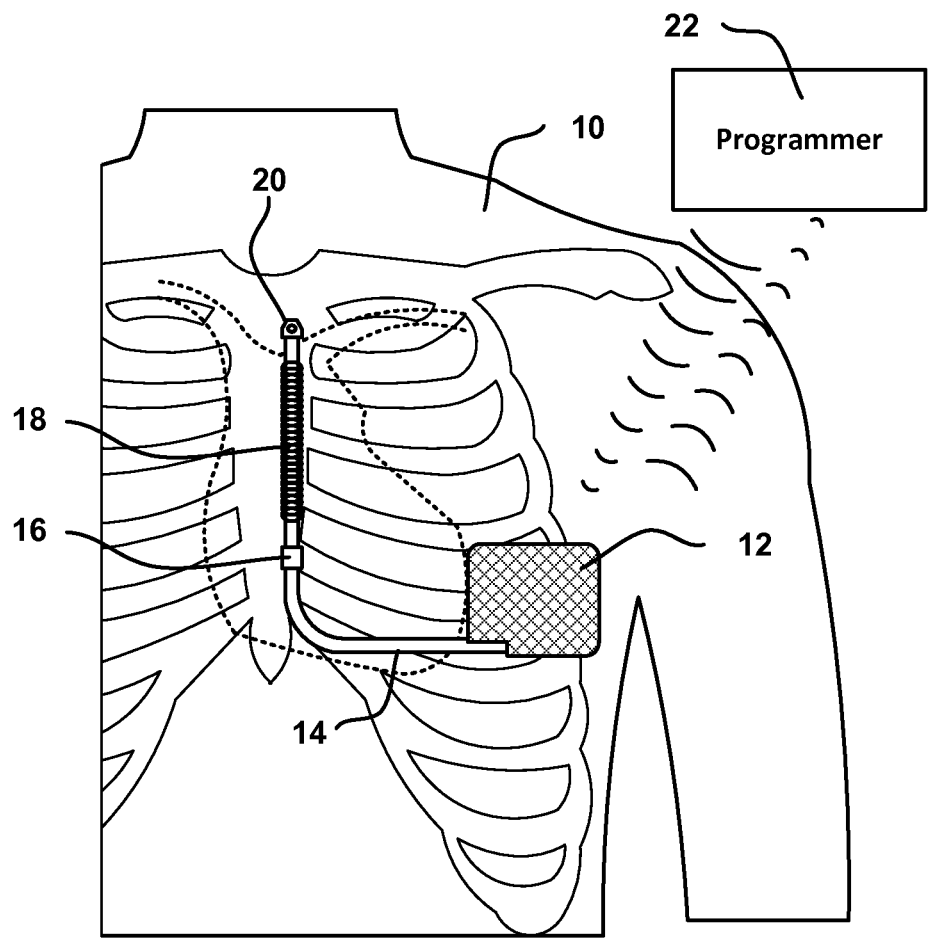
FIG. 1 illustrates a possible position of a subcutaneous cardiac device system forming several sensing vectors.

FIG. 1 illustrates a subcutaneous cardiac device system forming several sensing vectors. The example system is implanted in a patient 10, over the patient's ribs and beneath the skin. A canister 12 is implanted, in the example, at approximately the left axilla (armpit), beneath the arm. A lead 14 extends from the canister 12 toward the patient's xiphoid and then over or slightly to the left of the sternum. The lead 14 includes electrodes 16, 18 and 20, with electrode 18 illustrated as a coil electrode designed primarily for shock delivery (though sensing via coil electrode 18 may be performed as well). The other electrodes 16 and 20 on lead 14 are shown as ring and cap electrodes, respectively. Other designs may be used. The canister 12, in this example, includes a conductive surface or, if desired, has an area on its surface which is conductive to allow for at least sensing of electrical signals and, when needed, therapy delivery.

Other configurations and implant locations may be used instead. Examples include right-sided or anterior-posterior subcutaneous implantation, transvenous systems, epicardial systems, intravascular systems, and other implementations such as drug pumps or neurostimulation systems that may incorporate cardiac signal analysis. Some alternatives and additional details are discussed below.

Figure 2:
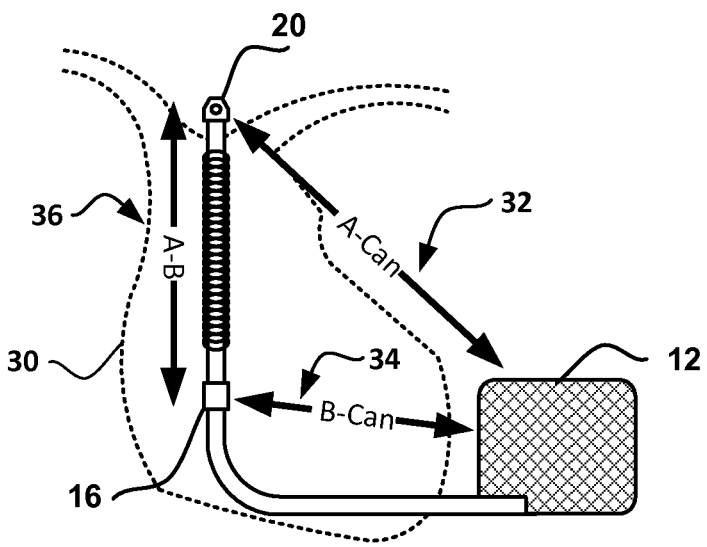
FIG. 2 highlights certain of the sensing vectors for the system of FIG. 1.

FIG. 2 highlights certain of the sensing vectors for the system of FIG. 1. Using the illustrative positioning shown in FIG. 1, the system provides sensing along three sensing vectors, which are shown relative to the heart 30. The vectors are labeled A-Can 32, between the distal electrode 20 and the canister 12, B-Can, between the proximal sensing electrode 16 and the canister 12, and A-B, between the distal sensing electrode 20 and the proximal sensing electrode 16. Additional sensing vectors may also be defined using the coil electrode 18 relative to the other electrodes 16, 20 or canister 12. As can be observed, each vector 32, 34, 36 provides a different "view" of the heart 30.

A cardiac cycle typically includes several portions (often referred to as "waves") which, according to well-known convention, are labeled with letters including P, Q, R, S, and T, each corresponding to certain physiological events. Each cardiac cycle usually has all of these parts, though not all may be visible on any given cardiac signal representation. Certain components may not be visible due to factors such as elevated rate, choice of sensing vector, anatomic anomaly, or active arrhythmia, for example. The combination of Q, R and S "waves" can be referred to as the QRS complex.

It has been shown (see, e.g., U.S. Pat. No. 7,392,085) that different sensing vectors provide different "views" of the cardiac cycle. For example, in one sensing vector, the R-wave may be much larger than the T-wave, while in another sensing vector, the differences between R-wave and T-wave will be less dramatic. Features may vary among patients and within a single patient, depending upon posture and activity level, among other factors. Sensing vector selection or optimization can be performed to provide an implantable system with the best opportunity to accurately assess the patient's cardiac rhythm. Some examples can be found in U.S. Pat. Nos. 7,623,909 and 8,200,341, the disclosures of which are incorporated herein by reference.

When detecting events, an implantable cardiac device may compare the sensed signal to a detection threshold. If/when the sensed signal crosses the detection threshold, a new detected event is declared. The detection threshold may be static or may change with time (or by dependence on other variables such as observed signal frequency, perceived noise, etc.), depending upon the system configuration. In some systems the detection threshold has a shape defined by a detection profile which can be applied anew after each detected event. Often the detection profile is configured for detecting R-waves or the QRS complex while passing over the rest of the cardiac cycle without making additional detections.

Figure 3:
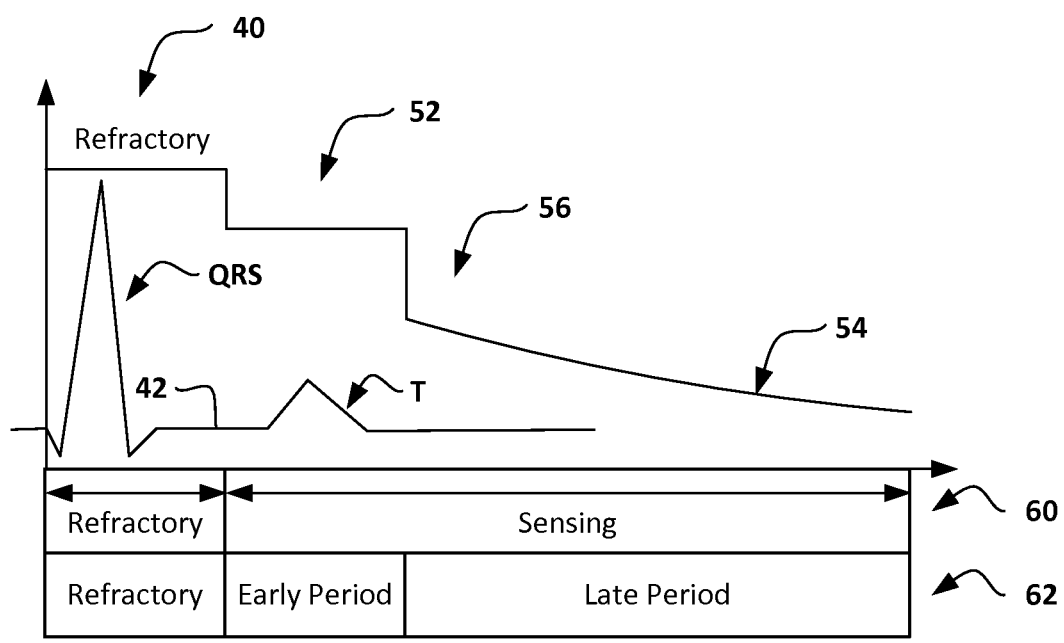
FIG. 3 illustrates a detection profile designed to identify cardiac events in a sensed signal.

FIG. 3 illustrates one such detection profile designed to identify cardiac events in a sensed signal. The detection profile shown in FIG. 3 is designed for detection of an R-wave or QRS complex. A refractory period 40 is provided at the far left of the figure (as is typical in the art, time progresses to the right in the figure, to match with the usual way of visually presenting cardiac signal data). An illustrative cardiac signal is provided at 42, including a QRS complex and a T-wave as marked.

The overall detection profile in FIG. 3 includes the refractory period 40 followed by an early detection stage 52 and a late detection stage 54. The refractory period is an initial time period that follows a threshold crossing. During the refractory period, captured signal data may be recorded and/or analyzed, but additional detected events are not declared. The refractory period helps avoid additional detections of the QRS complex once it has been detected.

The refractory period 40 may have a duration of, for example, 100 to 250 milliseconds, with illustrative examples of about 160 and 200 milliseconds, for example, in some subcutaneous systems. Depending upon the signal being captured, a shorter refractory period may be used, for example, a refractory period of 70-150 milliseconds may be used for a transvenous sensing vector, which will see a "narrower" QRS complex in a near-field vector, typically, than a subcutaneous sensing vector. Other durations may be used.

The early stage 52 is shown as having a constant threshold for a period of time. In one example, the early stage may be in the range of 100 to 400 milliseconds long, with a threshold that is a fixed voltage or a fixed percentage of the overall amplitude (peak) of the QRS, or an average of several peaks, or other measure. Next, a decaying threshold is used in the late period 54, for example, beginning from a fixed voltage or a percentage of the overall amplitude (peak) of the QRS, or an average of several peaks, or other measure, and decaying, using, for example, an exponential decay, to a lower limit such as the sensing threshold of the system.

Some illustrative detection profiles are shown in U.S. Pat. No. 8,565,878, titled ACCURATE CARDIAC EVENT DETECTION IN AN IMPLANTABLE CARDIAC STIMULUS DEVICE, and U.S. Pat. No. 5,709,215, titled R-WAVE DETECTION METHOD OF IMPLANTABLE CARDIOVERTER DEFIBRILLATORS, the disclosures of which are incorporated herein by reference.

Two sets of terminology are illustrated in FIG. 3. In a first example, the detection profile includes a refractory period followed by a sensing period, as shown at 60. In a second example, a refractory period is followed by an early sensing period and a late sensing period, as shown at 62. In one illustration, the early period is designed to ensure that the T-wave will occur before it expires. For example, if the refractory period has a length of 160 milliseconds, then the early period may have a duration in the range of 140 to 340 milliseconds. In one example, the length of time covered by the refractory period and the early period is about up to 500 milliseconds, long enough to capture the T-wave in most signals.

The overall sensing period in example 60, or the combination of early and late periods in example 62, may have durations of up to or more than one second. In another example, the overall sensing period plus refractory in example 60, or the combination of refractory, early period and late period in example 62 may add up to one second of duration. Different durations may be used, if desired. In one example, the overall length of refractory plus sensing in example 60, or the overall length of refractory plus early and late periods in example 62, is defined by the interval between consecutive detected events.

The specifics of a detection profile can vary widely, and the U.S. Pat. No. 8,565,878 provides several illustrative examples and points out numerous variants and modifications, as does the U.S. Pat. No. 5,709,215.

The detection profile of FIG. 3 is provided to assist in understanding the calculations performed in an illustrative method of vector analysis and selection. In an example, certain peaks are measured for a given cardiac signal and compared to one another, to thresholds, or such peaks as measured in several vectors may be compared, or a combination thereof, as illustrated in FIGS. 4A-4B.

Figure 4A:
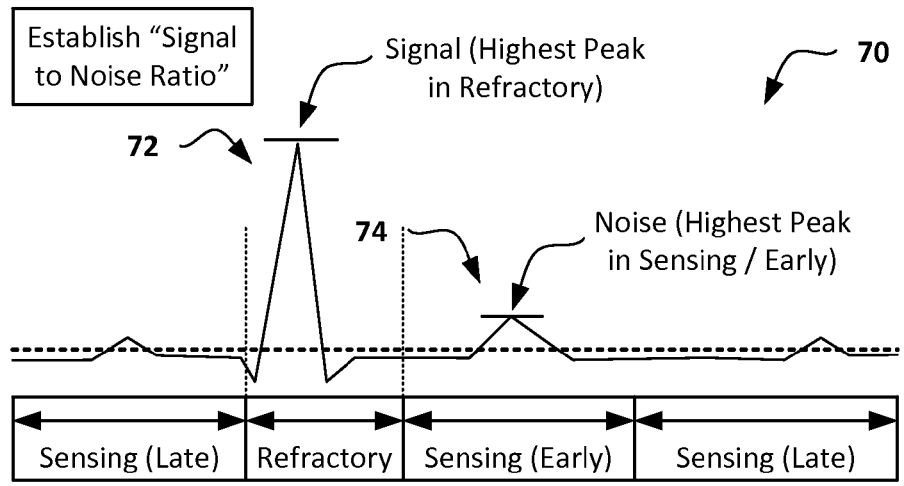
FIGS. 4A-4B illustrate an approach to sensing vector selection.
Figure 4A:
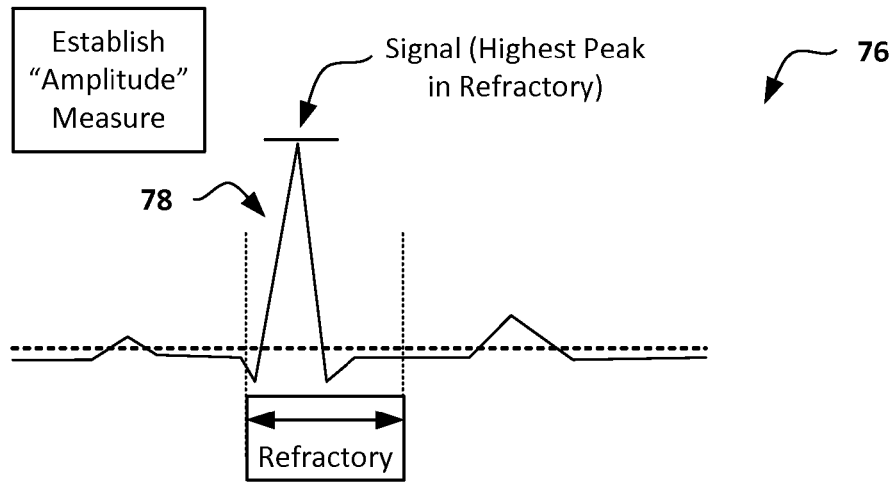
Figure 4B:
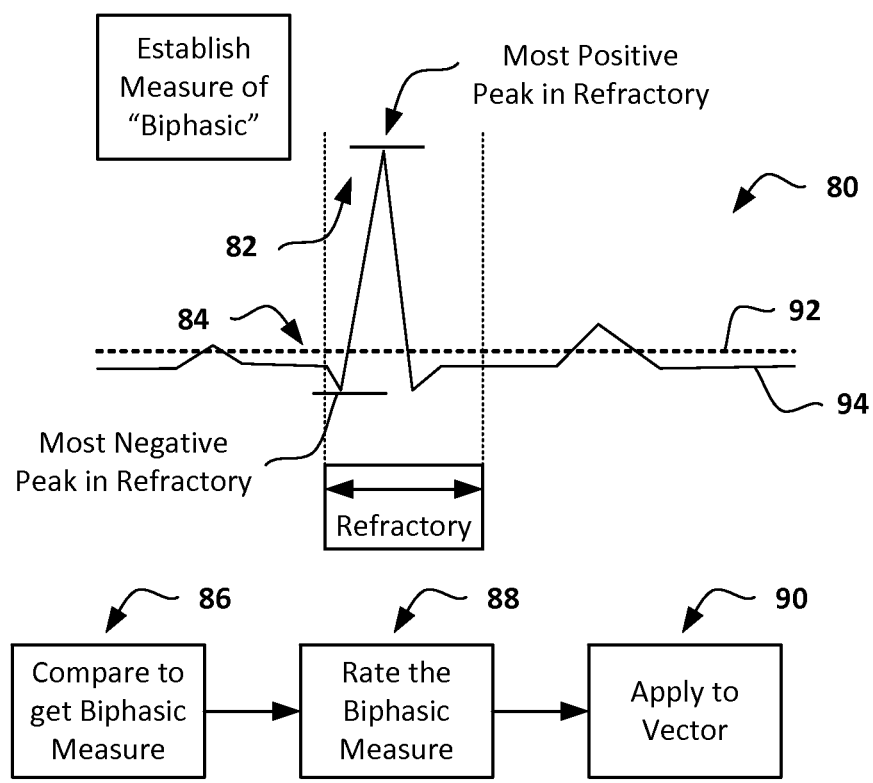

FIGS. 4A-4B illustrate an approach to sensing vector selection. FIG. 4A illustrates some of the features suggested in U.S. Pat. No. 7,623,909, titled IMPLANTABLE MEDICAL DEVICES AND PROGRAMMERS ADAPTED FOR SENSING VECTOR SELECTION, the disclosure of which is incorporated herein by reference.

Referring now to FIG. 4A, steps to establish a signal to noise ratio are shown at 70. A "signal" is measured as the highest peak in the refractory period, as indicated at 72. The "noise" is measured as the highest peak in the "early" stage of the sensing profile, as shown at 74, if using the terminology as shown at 62 in FIG. 3. Alternatively, the "noise" may be measured as the highest peak during the overall sensing time period following refractory, if using the terminology of the example at 60 in FIG. 3.

Using the signal and noise values, a signal to noise ratio (SNR) can be calculated, typically by division of the measured signal amplitude by the measured noise amplitude, though other versions of SNR may be used. Given that implantable systems are power constrained, sometimes simplified versions of a calculation may be chosen in place of more calculation intensive versions (i.e., subtraction rather than division). For example, SNR could be calculated by simple subtraction, by adding or subtracting an offset to one or the other of the measured signal or noise value before division, by use of a look-up table, or otherwise. In one example, simple division is used to calculate the SNR, and a look-up table is used to evaluate the meaning of the SNR to vector selection once calculated.

Steps to establish an amplitude measure are shown at 76. In the illustrative example, the highest peak signal in refractory is calculated, as shown at 78. An alternative example may consider both the height and width of the peak signal during refractory. The "Amplitude" measure may be a signed or unsigned value, depending on design preference. The use of a combination of SNR and amplitude is discussed in the U.S. Pat. No. 7,623,909 as a means to generate a "SCORE" indicating the qualities of the cardiac signal vector under analysis. Additional enhancements to a scoring approach are discussed in U.S. Pat. No. 7,783,340, titled SYSTEMS AND METHODS FOR SENSING VECTOR SELECTION IN AN IMPLANTABLE MEDICAL DEVICE USING A POLYNOMIAL APPROACH, the disclosure of which is incorporated herein by reference.

Turning now to FIG. 4B, some illustrative examples add another variable to the calculus by considering a measure of the "Biphasic" nature of the detected signal for a given vector. A signal that has a peak that is much larger in one polarity than in the opposite polarity relative to a baseline or quiescent point is considered not biphasic; a signal that has similar peaks on each side of the baseline or quiescent point is considered biphasic. In some examples, whether the cardiac signal is biphasic is determined based primarily on the QRS complex. In other examples, the entire cardiac cycle may be considered, or the QRS complex plus the T-wave can be assessed.

To establish a measure of how biphasic the signal is, the example shown at 80 identifies the most positive peak during the refractory period, as shown at 82, and also identifies the most negative peak during the refractory period, as shown at 84. These peaks 82, 84 are then compared at 86. Thus, this example focuses on whether the QRS portion of the cardiac cycle is biphasic. Other examples may look beyond the QRS portion of the cardiac cycle for biphasic characteristics, for example, if the T-wave is opposite in polarity to the largest peak of the QRS complex, this may be determined by expanding the search time-frame for peaks to include both the QRS as well as the T-wave.

In one example, a Biphasic Measure is calculated at block 86. The Biphasic Measure from block 86 is then rated using, for example, a look-up table or a calculation such as a polynomial or other formula, as shown at 88. The outcome of these steps 86, 88 is then incorporated in the vector selection calculation, as shown at 90.

In one example, the Biphasic Measure is calculated as a ratio of the most positive and most negative peaks from the refractory period. In another example, the peaks 82, 84 may be subtracted one from the other. Other calculations may be used. In one example, rather than the most positive and most negative peaks, instead, the largest overall peak may be chosen, and the largest peak of the opposing polarity that immediately precedes (or follows, in another example) the largest overall peak is chosen for use in comparison.

Certain examples herein disfavor a biphasic signal because it can create difficulties in the calculation of correlation. In an example, a signal analysis system compares the shape of two signals by selecting the largest peak of each signal as an alignment point. A monophasic signal will predictably select the same peak each time; a biphasic signal may dither between selecting the positive or negative peak, if the "largest" peak is sometimes positive and other times negative relative to baseline. Such a system may favor the monophasic signal to more predictably perform correlation analysis.

In an alternative example, a biphasic signal may be favored due to the ability to balance the signal about a quiescent point. A typical approach to maintaining the baseline/quiescent point of the system is to periodically correct the analog-to-digital converter output so that the average output over a relatively long period is treated as the baseline or "zero". For a monophasic signal, a larger share of the cardiac signal power, particularly the QRS complex, is on one side of the isoelectric line, such that the cardiac signal isoelectric line and the baseline/quiescent point may not be the same. This phenomenon can be observed in FIG. 4B where, as shown at 92 and 94, the baseline 92 is slightly elevated above the isoelectric line 94 of a monophasic cardiac signal. Selecting a more biphasic signal vector places the isoelectric line 94 closer to the baseline 92 in the selected vector.

There may be other reasons to favor or disfavor biphasic signals as well, often driven by unique features of a given implementation and/or hardware.

Figure 5:
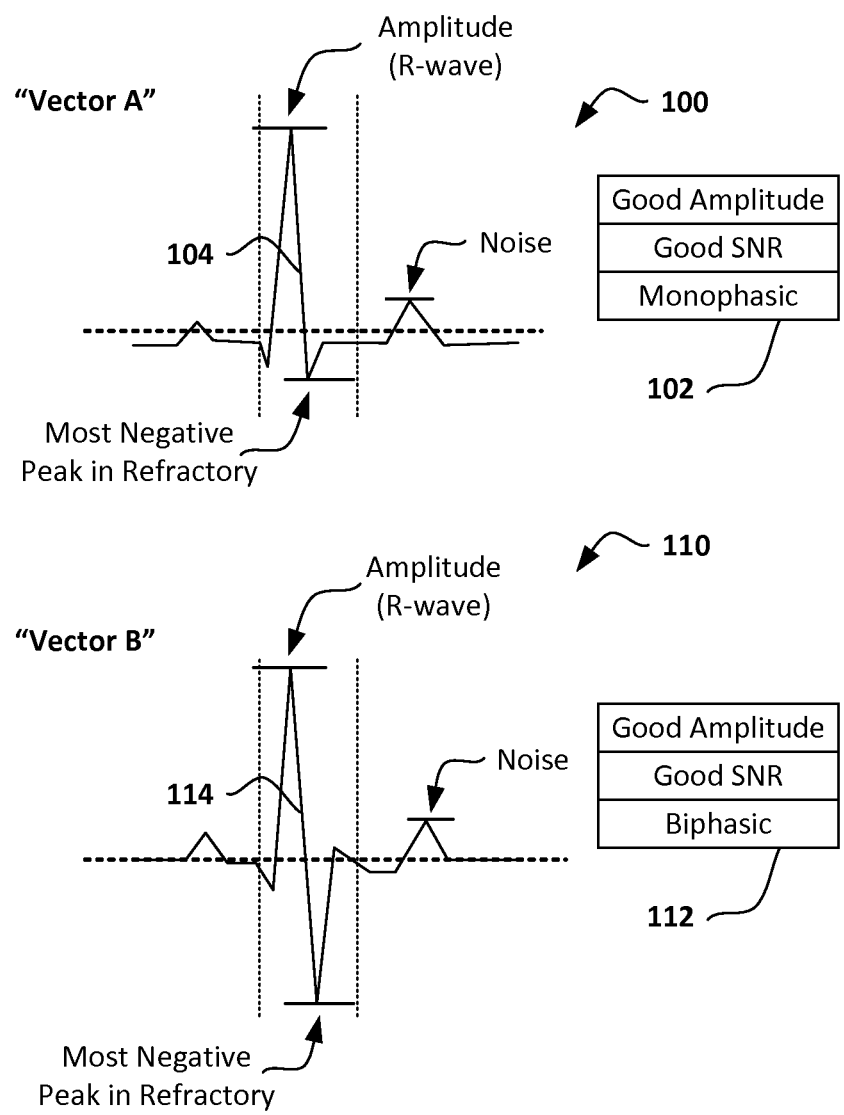
FIG. 5 demonstrates the application of the sensing vector selection approach of FIGS. 4A-4B to cardiac signals.

FIG. 5 demonstrates the application of the sensing vector selection approach of FIGS. 4A-4B to cardiac signals. For a first sensing vector, "Vector A", the signal is visibly monotonic, as illustrated at 100. The positive amplitude peak during refractory (refractory is indicated by the two vertical lines) is larger than the most negative peak during refractory by a significant margin, and is also well larger than the noise peak noted outside of refractory. As indicated at 102, this signal is considered in the system to have a good amplitude, good SNR, and monophasic shape.

In contrast, "Vector B", shown at 110, is visibly biphasic. The positive amplitude peak during refractory (again indicated by two vertical lines) is larger than the noise peak noted outside of refractory by a wide margin. The amplitude of the most positive peak in refractory is similar to the amplitude of the most negative peak during refractory. As shown at 112, the signal has good amplitude and good SNR, but is identified as biphasic.

The distinction between monophasic and biphasic, in the illustrative embodiment, can be defined in several ways. Some examples are shown in the table, where "LP" indicates the absolute value of the amplitude of the larger peak of the largest positive and largest negative peaks during refractory, and "SP" indicates the absolute value of the smaller peak of the largest positive and largest negative peak during refractory. In this table, ST indicates the absolute sensing threshold of the system:

| Illustrations: | Monophasic | Biphasic | Other |
|---|---|---|---|
| Example 1 | LP > 3 * SP | LP < 2 * SP | All else |
| Example 2 | (LP − SP) > 500 µV | (LP − SP) < 250 µV | All else |
| Example 3 | LP > 2 * SP | All else | n/a |
| Example 4 | LP > 6 * ST AND LP > 1.5 * SP | All else | n/a |

Thus, some examples are based on the size ratio between LP and SP, some are based on absolute differences, and at least one example integrates a requirement related to the absolute sensing threshold of the system. Some examples use three categories (Monophasic/Biphasic/Other) and other examples use just two categories (Monophasic/Biphasic).

In some examples, categorical statements about whether the signal is biphasic or monophasic may drive the analysis. For example, a system could select the least biphasic sensing vector for use in cardiac signal analysis. In other examples shown below, the biphasic nature of the signal is integrated into a variable that is included in the analysis. For example, biphasic-ness may be but one of several signal characteristics brought into consideration when selecting sensing vector(s).

In the illustration of FIG. 5, the biphasic nature of the signal is analyzed by performing calculations on positive and negative signal excursions occurring in the vicinity of the QRS complex. In some illustrative examples, noise elements or artifacts in the cardiac signal are not contemplated as providing indications the biphasic nature of the signal, thus, T-waves and the S-T segment (or elevation thereof) are not considered and may be excluded from the analysis. For example, a system may consider the biphasic nature of the cardiac signal for vector selection purposes by omitting signal more than a predefined time period away from the R-wave, such as 200 milliseconds.

Bazett's formula, as well as various similar calculations (Fridericia's formula or the regression model from Sagie et al.), can be used to estimate the time at which a T-wave would occur following a QRS complex given a particular rate (Bazett postulates that the ratio of QT interval to the square root of the average R-R interval is fixed for a given patient). If desired, a system may use Bazett's formula or other calculations in combination with the observed cardiac rate to establish a limit on the quantity of signal to analyze for biphasic nature, though generally speaking a fixed window may be simple and fairly reliable.

For example, according to Fridericia's formula, a "normal" QT at 60 beats-per-minute is about 400 milliseconds and the QT interval for the same patient at 180 beats-per-minute (BPM) would be 277 milliseconds, and at 240 bpm, the QT interval would narrow to 251 milliseconds. Since QRS width greater than 120 milliseconds is considered "wide," a 200 millisecond window allows ample time for the entire QRS complex without bringing T-waves into the analysis.

As noted above, in some alternative examples, the QRS complex plus the T-wave is considered in an assessment of whether a signal is biphasic. In further examples, the entire cardiac cycle may be assessed when determining whether the cardiac signal is biphasic. In another example, the assessment of whether a signal is biphasic is based on comparing the peaks at opposing ends of the longest monotonic segment (a segment lacking turning points is monotonic; here, length is defined as amplitude change) in the refractory (or other) period. The longest monotonic segment is shown at 104 and 114, respectively, in the Vector A and Vector B illustrations of FIG. 5.

In some examples, the three factors noted at 102 and 112 are combined to generate an overall quality metric for each of Vector A and Vector B. In one example, each of the three factors is assessed to provide three variables which can be multiplied or summed to yield an overall quality metric. In another example, the three factors are compared to pass/fail boundaries for each metric and if all three factors pass individually, a combined metric is then calculated. When multiplying or summing the three variables, one factor may be more heavily or lightly weighted than the others. The factors may be graded according to a continuum or look-up table, or by use of a polynomial. Additional or different factors may also be used.

For example, U.S. Pat. No. 7,783,340 describes a method of vector selection that generates a pair of scoring factors related to amplitude (Sa) and SNR (Sr). Those factors are then multiplied to generate a total score for a vector. In an illustrative example, a similar approach can be taken to generating Sa and Sr using a polynomial or a look-up table, if desired. In addition, a third factor related to the biphasic nature of the signal can be calculated as Sb. The "score" for a sensing vector can then be calculated as Sa*Sb*Sr, as Sa+Sb+Sr, or, in another example, as (Sa*Sr)+Sb. Other combinations can be used.

In one example, Sa, Sr and Sb are all scaled to values from 1 to 10 and multiplied together to give a result in a range of 1 to 1000. In another example, Sa and Sr again are scaled to values between 1 and 10 and their product has a range of 1 to 100. Sb can be scaled to a range of 0 to 10, but is instead added to the product of Sa and Sr, giving the total outcome a range from 1 to 110. Other scales and scoring methods can be used.

In another example, Sb may be considered only if both Sa and Sr exceed a lower threshold in each of the vectors under consideration, or if the product of Sa and Sr in every vector under consideration meets some threshold. In this version, Sb would be used to distinguish among known "good" vectors, but could not promote a relatively poor vector in terms of amplitude and SNR above other, better vectors for amplitude and SNR. This is in part because, in this example, the monophasic or biphasic signal features provide an advantage for discriminating one arrhythmia from another, but accurate sensing, reliant on SNR and amplitude, is needed to get to the rhythm discrimination stage in the first place.

Numerically, here are certain examples:

In a first example, given an input range of up to 2.5 millivolts (mV), with a sensing floor at 0.1 mV, Sa is ten times the difference between the maximum amplitude (in mV) of the peak in refractory less 0.2 mV (giving a range from 0 to 23); Sr equals thrice the maximum amplitude (in mV) during refractory divided by the maximum peak outside of refractory with a maximum value of 10; and Sb equals ten divided by the difference between the absolute value of the maximum positive and negative peaks during refractory (in mV), with a maximum value of 10; the output "score" of the sensing vector is zero if Sa*Sr is less than 5, and is otherwise equal to the sum of Sb plus Sa*Sr. This first example favors sensing vectors with biphasic signals, as the difference between the absolute values of the positive and negative peaks would be smaller when biphasic making Sb larger.

In a second example, a selectable gain that can accommodate a 1.8 mV maximum signal at X2 gain and a 3.6 mV gain at X1 gain, Sa, Sr and Sb are taken from a lookup table. The vector "score" is the product of Sa*Sr*Sb. The lookup table is as follows, where "Ratio" is calculated as the ratio of the absolute value of the greatest positive amplitude during refractory divided by the greatest negative amplitude during refractory:

| Sa  | Amplitude (mV) | Sr  | SNR     | Sb  | Ratio   |
|-----|----------------|-----|---------|-----|---------|
| .5  | ≤0.5           | 0.5 | ≤3      | 10  | >4      |
| 5   | 0.5-0.65       | 1   | 3.0-3.5 | 8   | 3.0-4.0 |
| 10  | 0.65-0.8       | 25  | 3.5-4.0 | 5   | 2.5-3.0 |
| 18  | 0.8-1.0        | 50  | 4.0-5.0 | 2   | 2.0-2.5 |
| 30  | 1.0-1.7        | 75  | 5.0-7.5 | 1   | 1.8-2.0 |
| 20  | 1.7-2.0        | 100 | >7.5    | .5  | <1.8    |
| 40  | 2.0-3.0        | —   | —       | —   | —       |
| 15  | 3.0-3.5        | —   | —       | —   | —       |
| 0.5 | 3.5-4.0        | —   | —       | —   | —       |

In a final set of examples, Sa and Sr are calculated using one or more polynomial formulas as disclosed in U.S. Pat. No. 7,783,340, titled SYSTEMS AND METHODS FOR SENSING VECTOR SELECTION IN AN IMPLANTABLE MEDICAL DEVICE USING A POLYNOMIAL APPROACH, the disclosure of which is incorporated herein by reference. For example, Sa can be calculated according to the formula graphed in FIG. 10A, or Sa can be calculated using the formula graphed in FIG. 10C, according to another example. Sr can be calculated according to the formula used to generate FIG. 10B. In this example, Sb is calculated as follows:

If the greater of the largest positive and negative peaks during refractory is more than four times as large as the lesser of the two, Sb is positive 250;

If the greater of the largest positive and negative peaks during refractory is between three and four times as large as the lesser of the two, Sb is positive 100;

If the greater of the largest positive and negative peaks during refractory is between two and three times as large as the lesser of the two, Sb is zero; and If the greater of the largest positive and negative peaks during refractory is less than twice as large as the lesser of the two, Sb is negative 250.

Where the final vector score is calculated by adding Sb to the product of Sa and Sr.

Figure 6:
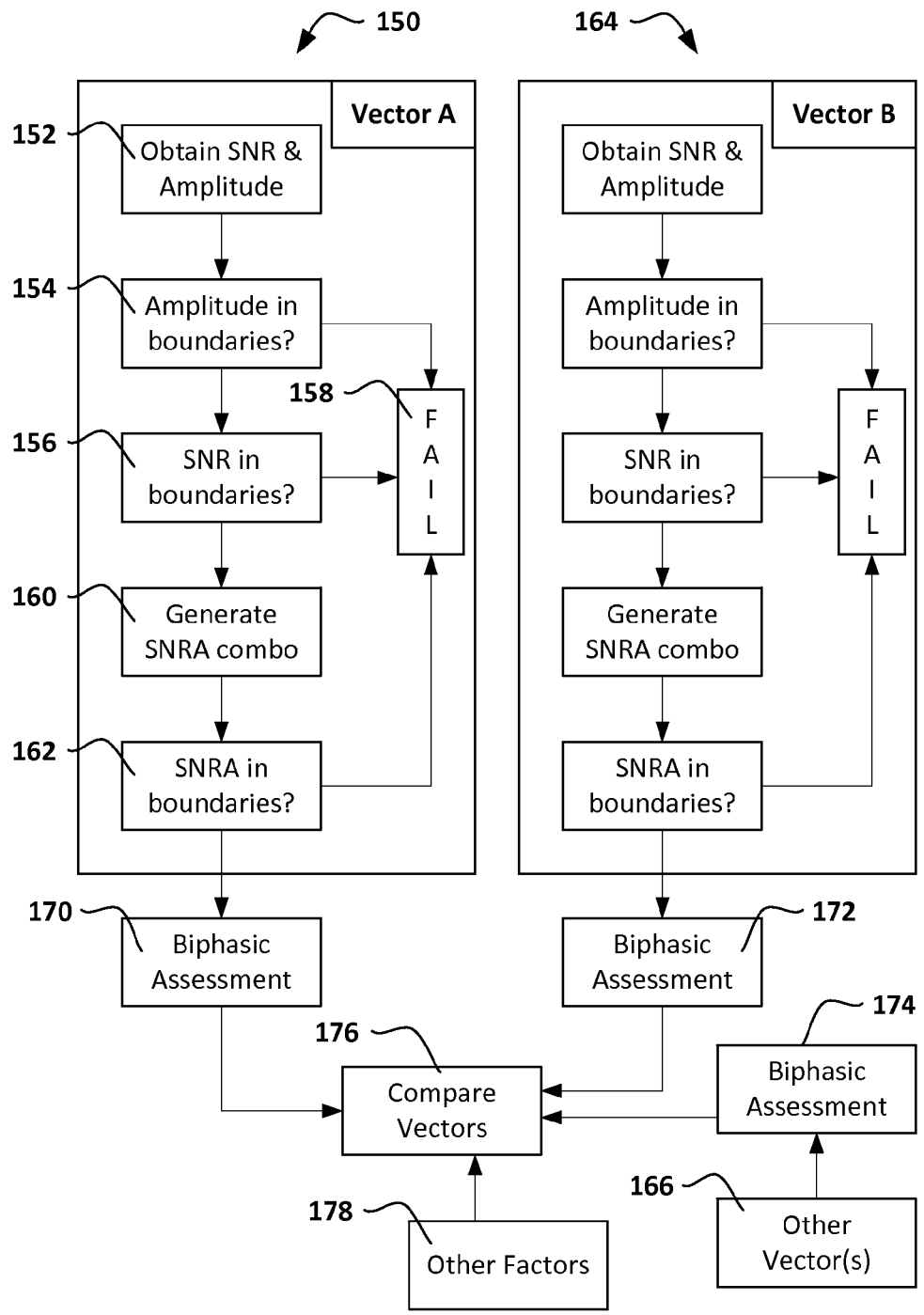
FIG. 6 shows an illustrative method of vector selection.

FIG. 6 shows the integration of several vectors being analyzed together, as well as an illustrative method. In this method, several tiers of checking and double checking the usefulness of sensing data are combined. In the illustration, sensing data is assessed for "Vector A" as shown at 150. The analysis begins with capturing a number of detected events to obtain SNR and Amplitude data. A single detected event could be captured and analyzed, but in most examples, several detected events are assessed together to provide averaged information as well as, if desired, the opportunity to identify and exclude outlier detections (such as ventricular extra-systolic events or premature ventricular contractions).

Once SNR and Amplitude data are captured at 152, the amplitude is compared to predefined boundaries at 154, as is the SNR at 156. If boundary conditions are not met, Vector A would fail the analysis, as shown at 158. Provision of separate screening and a failure outcome at 158 can be omitted in some examples. In the illustration shown, the inclusion of blocks 154 and 156 is intended to screen out sensing vectors having unsuitably small or large amplitudes and/or unsuitably low SNR.

After separately assessing amplitude and SNR, the method next generates a combination factor, SNRA, combining features for SNR and Amplitude together, as shown at 160. SNRA is compared to boundary conditions as well, as shown at 162 and, again, the vector may fail 158. In some examples, blocks 160 and 162 are omitted.

Using steps 152 to 162, the overall, general suitability of Sensing Vector A can be assessed. Similar steps would apply as well to Vector B 164, and other vectors 166. Upon finding that a vector is generally suitable for use, the method then proceeds to use biphasic assessments at 170, 172 and/or 174 to further inform the selection of a "best" vector in a comparison step at 176. If desired, boundary conditions to the biphasic nature of the signal may be applied as well, and one or more vectors may fail to reach the comparison at 176 on that basis. In some examples, a single "best" vector may be selected as a default vector for the implantable system. In other examples, two vectors may be selected for use in tiered or cooperative analysis.

In some examples, the "fail" block 158 may be omitted, and all vectors passed to the comparison block 176. In another example, the comparison block 176 may not be reached if a vector under analysis is found to have excellent sensing capabilities, allowing a bypass of additional vector selection analysis once a highly suitable sensing vector has been identified. For implantable systems, the opportunity to bypass further analysis once a "good" vector has been found may allow energy savings.

In addition to the consideration of "Biphasic" nature of the cardiac signal, other factors may be introduced as well or instead, as noted at block 178 of FIG. 6. In one example, the number of maximum slope points or inflection occurring during refractory (or other period) is counted for detected events and a Turning Point score or Inflection Point score is calculated. A higher number of turning points or inflection points suggests a signal that may appear to the detection apparatus to be noisy, and so a sensing vector with cardiac signals having a larger number of such points can be disfavored over one with fewer such points. In another embodiment, a minimum path length is defined and only those turning points or inflection points that follow a minimum path length since the last such point, or which are followed by a minimum path length without another such point, are counted.

In another example, beat-to-beat similarity may be incorporated to generate another score. For example, largest peaks for a number of consecutive detected events can be assessed (using, for example, sum of differences, variance or standard deviation, or maximum to minimum largest peak difference), and a score generated from the measure of beat to beat amplitude variation. A sensing vector with greater variability may be disfavored over a sensing vector with less variability. This may be useful, in particular, where sensing vector selection is performed in a controlled environment where the patient is sitting still or where the patient is known to be exercising. The patient may be asked to perform certain tasks (walking, exercise testing such as running, or the Valsalva maneuver, for example), or to breathe deeply during vector analysis to accentuate any such variability.

These additional factors may be assessed, as above, using a formula or a lookup table, as desired. Such factors may be an additional assessment once vector suitability is established, or may be integrated into analysis from the start.

The above methods and systems may be used to perform sensing vector selection of a default or primary sensing vector. A second or alternative sensing vector may also be chosen. In some systems, two sensing vectors are chosen for simultaneous use. In some systems, sensing vector selection may be used to select a "morphology" or far field vector, for use in conjunction with a rate vector, such as in a transvenous system having a rate channel configured to sense the R-wave, with a far field vector being selected from several options to allow discrimination.

Referring briefly again to FIG. 1, certain potential design elements will be described. The canister 12 typically contains circuitry for communication with the programmer 22. Communication may be inductive, RF or via any other suitable medium of communication. Such communication can be useful to configure the implanted system for sensing, therapy or other feature, to load new software or firmware for the implanted system, and to retrieve information about system operation such as device status, therapy history, diagnostic data (both device and patient related), or other suitable data. In some examples, sensing vector configuration can be performed using the programmer 22 communication feature. In some examples, the implanted system performs sensing vector configuration independently according to a schedule or in response to an event, for example.

The canister 12 preferably contains operational circuitry for the implantable system. The operational circuitry may include a controller and any suitable analog and/or digital circuits needed for signal processing, memory storage and generation of high-power electrical, low-power electrical and/or non-electrical outputs. The operational circuitry may be coupled to suitable battery technology for an implantable device, with any of numerous examples well known in the art, and may use various capacitor technologies to assist in the short term build-up and/or storage of energy for defibrillation or other high output purposes.

The operational circuitry may include, for example, a set of switches, a switch matrix, or a multiplexer, to select inputs from among the various sensing vectors. Before and/or after signals reach the vector-selecting switches, matrix or multiplexer, analog to digital conversion and/or filtering can be applied. One or more vectors may be selected. In one example, the present invention may be used to establish a hierarchy within vectors, such that the system can use a first vector to determine whether a treatable cardiac rhythm is occurring, and turns to additional vectors if a conclusion cannot be reached. In other examples, a single vector is selected. In some examples, multiple vectors can be selected for combination in signal processing, as needed, or for use in other suitable methods.

The lead 14 and external shell for the canister 12 can be manufactured with various materials suitable for implantation, such as those widely known, along with coatings for such materials, throughout the art. For example, the canister 12 can be made using titanium, with a titanium nitride or iridium oxide (or other material) coating if desired, and the lead can be formed with a polymeric material such as a polyether, polyester, polyamide, polyurethane or polycarbonate, or other material such as silicon rubber. The electrodes 16, 18, and 20 can be formed of suitable materials as well, such as silver, gold, titanium or stainless steel such as MP35N stainless steel alloy, or other materials.

The location of system implant may vary. For example, the system shown is a subcutaneous-only system located on the anterior and lateral chest between the skin and ribcage of the patient. Other subcutaneous only systems (including systems without a lead 14, with multiple leads 14, or an array in place of lead 14) may be used with other anterior only placements and/or anterior-posterior, posterior only, left-right, etc. locations, including, for example, locations noted in U.S. Pat. Nos. 6,647,292, 6,721,597, 7,149,575, 7,194,302, each of which is incorporated herein by reference, and other locations as well. Subcutaneous placement can include any location between the skin and ribcage, including sub-muscular.

Other systems may include one or more transvenous leads or epicardial leads/electrodes, and may use different canister implant locations, such as placing the canister in a higher pectoral position closer to the clavicle for closer venous access, or abdominal placement. Illustrative transvenous systems include single chamber, dual chamber and biventricular systems. A fully intravenous system has also been proposed. Additional or other coatings or materials than those noted above may be used, particularly for epicardial, transvenous or intravenous systems, leads and canisters.

Various alternatives and details for these designs, materials and implantation approaches are known to those skilled in the art. Commercially available systems in which the above methods can be performed or which may be configured to perform such methods are known including the Boston Scientific Teligen® ICD and S-ICD® System, Medtronic Concerto® and Virtuoso® systems, and St. Jude Medical Promote® RF and Current® RF systems.

A first illustrative example takes the form of a method of sensing vector selection in an implantable cardiac device, the implantable cardiac device including electrodes configured for sensing electrical signals while implanted coupled to operational circuitry configured for analyzing signals captured from the sensing electrodes, wherein the operational circuitry and electrodes are configured to define at least two sensing vectors for sensing cardiac signals, the method comprising, for a first sensing vector, the operational circuitry establishing each of: an estimate of signal-to-noise ratio; an estimate of cardiac signal amplitude; and a measure of biphasic or monophasic nature of sensed signals; and the operational circuitry combining the signal to noise ratio, cardiac signal amplitude and measure of biphasic or monophasic nature of sensed signals to generate a sensing quality metric for the first sensing vector.

A second illustrative example builds on the first illustrative example and further comprises, for the first sensing vector, the operational circuitry sensing a plurality of cardiac cycles with selected electrodes by applying a detection profile to a sensed cardiac signal to detect a cardiac cycle, wherein the detection profile includes a refractory period and a sensing period, the refractory period being applied to a first portion of the cardiac cycle and the sensing period being applied to at least a second portion of the cardiac cycle; wherein the step of the operational circuitry establishing an estimate of cardiac signal amplitude comprises the operational circuitry analyzing a sensed amplitude from the first portion of the cardiac cycle for each of several cardiac cycles.

A third illustrative example builds on the first illustrative example and further comprises, for the first sensing vector, the operational circuitry sensing a plurality of cardiac cycles with selected electrodes by applying a detection profile to a sensed cardiac signal to detect a cardiac cycle, wherein the detection profile includes a refractory period and a sensing period, the refractory period being applied to a first portion of the cardiac cycle and the sensing period being applied to at least a second portion of the cardiac cycle; wherein the step of the operational circuitry establishing an estimate of signal to noise ratio includes the operational circuitry comparing a sensed amplitude from the first portion of the cardiac cycle to a sensed amplitude from the second portion of the cardiac cycle for each of several cardiac cycles.

A fourth illustrative example builds on the first illustrative example and further comprises for the first sensing vector, the operational circuitry sensing a plurality of cardiac cycles with selected electrodes by applying a detection profile to a sensed cardiac signal to detect a cardiac cycle, wherein the detection profile includes a refractory period and a sensing period, the refractory period being applied to a first portion of the cardiac cycle and the sensing period being applied to at least a second portion of the cardiac cycle; wherein the step operational circuitry establishing a measure of biphasic or monophasic nature of cardiac cycles comprises the operational circuitry comparing a sensed positive amplitude from the first portion of the cardiac cycle to a sensed negative amplitude from the first portion of the cardiac cycle for each of several cardiac cycles.

A fifth illustrative example builds on the first illustrative example and further comprises, for the first sensing vector, the operational circuitry sensing a plurality of cardiac cycles with selected electrodes by applying a detection profile to a sensed cardiac signal to detect a cardiac cycle, wherein the detection profile includes a refractory period and a sensing period, the refractory period being applied to a first portion of the cardiac cycle and the sensing period being applied to at least a second portion of the cardiac cycle; wherein the step operational circuitry establishing a measure of biphasic or monophasic nature of cardiac cycles comprises the operational circuitry comparing an average sensed positive amplitude from the first portion of several of the cardiac cycles to an average sensed negative amplitude from the first portion of several of the cardiac cycles.

A sixth illustrative example builds on the first illustrative example, wherein the step of the operational circuitry combining the signal to noise ratio, cardiac signal amplitude and measure of biphasic or monophasic nature of cardiac signals to generate a sensing quality metric for the first sensing vector comprises the operational circuitry finding the sum or product of: a first metric related to the signal to noise ratio; a second metric related to the cardiac signal amplitude; and a third metric related to the measure of biphasic or monophasic nature of cardiac signals.

A seventh illustrative example builds upon the first illustrative example, wherein the step of the operational circuitry combining the signal to noise ratio, cardiac signal amplitude and measure of biphasic or monophasic nature of cardiac signals to generate a sensing quality metric for the first sensing vector comprises the operational circuitry establishing a sensing vector score for the first vector using the signal to noise ratio and the cardiac signal amplitude, and adjusting the score in view of the measure of biphasic or monophasic nature of cardiac signals.

An eighth illustrative example builds on the first illustrative example and further comprises, for a second sensing vector, the operational circuitry establishing each of: an estimate of signal-to-noise ratio; an estimate of cardiac signal amplitude; and a measure of biphasic or monophasic nature of sensed signals; and the operational circuitry combining the signal to noise ratio, cardiac signal amplitude and measure of biphasic or monophasic nature of sensed signals to generate a sensing quality metric for the second sensing vector; and the operational circuitry using the sensing quality metrics for the first and second sensing vectors to select from at least the first and second sensing vectors a sensing vector for use in cardiac signal analysis.

A ninth illustrative example takes the form of a method of sensing vector selection in an implantable cardiac device, the implantable cardiac device including electrodes configured for sensing electrical signals while implanted coupled to operational circuitry configured for analyzing signals captured from the sensing electrodes, wherein the operational circuitry and electrodes are configured to define at least two sensing vectors for sensing cardiac signals, the method comprising: for the first sensing vector, the operational circuitry establishing a measure of biphasic or monophasic nature of cardiac signals; the operational circuitry selecting a default sensing vector for use in the analysis of cardiac signals using at least one factor related to the measure of biphasic or monophasic nature of cardiac signals generated for the first sensing vector.

A tenth illustrative example builds on the ninth illustrative example and further comprises the operational circuitry combining the measure of biphasic or monophasic nature of cardiac signals for the first sensing vector with at least one other factor related to the signals captured via the first sensing vector to generate a sensing quality metric for the first sensing vector.

An eleventh illustrative example builds on the ninth illustrative example, wherein the step of establishing a measure of biphasic or monophasic nature of cardiac signals comprises: identifying a QRS portion of a cardiac cycle; and comparing a positive peak in the QRS portion of the cardiac cycle to a negative peak in the QRS portion of the cardiac cycle.

A twelfth illustrative example builds on the ninth illustrative example, wherein the step of establishing a measure of biphasic or monophasic nature of cardiac signals comprises: detecting an event in a signal sensed along the first sensing vector; defining a window associated with the detected event; and comparing a positive peak in the window to a negative peak in the window.

A thirteenth illustrative example takes the form of an implantable cardiac device comprising: a plurality of electrodes configured for sensing electrical signals while implanted; and operational circuitry configured for analyzing signals received from the sensing electrodes. In the thirteenth illustrative example, the operational circuitry and electrodes are configured to define at least two sensing vectors for sensing cardiac signals and the operational circuitry is configured to perform the following: for a first sensing vector, calculating each of: an estimate of signal-to-noise ratio; an estimate of cardiac signal amplitude; and a measure of biphasic or monophasic nature of sensed signals; and combining the signal to noise ratio, cardiac signal amplitude and measure of biphasic or monophasic nature of sensed signals to generate a sensing quality metric for the first sensing vector.

A fourteenth illustrative example builds on the thirteenth illustrative example, wherein the operational circuitry is further configured to sense a plurality of cardiac cycles with selected electrodes for the first vector by applying a detection profile to a sensed cardiac signal to detect a cardiac cycle, wherein the detection profile includes a refractory period and a sensing period, the refractory period being applied to a first portion of the cardiac cycle and the sensing period being applied to at least a second portion of the cardiac cycle; and the operational circuitry is configured to calculate the estimate of cardiac signal amplitude by analyzing a sensed amplitude from the first portion of the cardiac cycle for each of several cardiac cycles.

A fifteenth illustrative example builds on the thirteenth illustrative example, wherein the operational circuitry is further configured to sense a plurality of cardiac cycles with selected electrodes for the first vector by applying a detection profile to a sensed cardiac signal to detect a cardiac cycle, wherein the detection profile includes a refractory period and a sensing period, the refractory period being applied to a first portion of the cardiac cycle and the sensing period being applied to at least a second portion of the cardiac cycle; and the operational circuitry is configured to calculate an estimate of signal to noise ratio by comparing a sensed amplitude from the first portion of the cardiac cycle to a sensed amplitude from the second portion of the cardiac cycle for each of several cardiac cycles.

A sixteenth illustrative example builds on the thirteenth illustrative example, wherein the operational circuitry is further configured to sense a plurality of cardiac cycles with selected electrodes for the first vector by applying a detection profile to a sensed cardiac signal to detect a cardiac cycle, wherein the detection profile includes a refractory period and a sensing period, the refractory period being applied to a first portion of the cardiac cycle and the sensing period being applied to at least a second portion of the cardiac cycle; and the operational is configured to calculate a measure of biphasic or monophasic nature of cardiac cycles by comparing a sensed positive amplitude from the first portion of the cardiac cycle to a sensed negative amplitude from the first portion of the cardiac cycle for each of several cardiac cycles.

A seventeenth illustrative example builds on the thirteenth illustrative example, wherein the operational circuitry is further configured to sense a plurality of cardiac cycles with selected electrodes for the first vector by applying a detection profile to a sensed cardiac signal to detect a cardiac cycle, wherein the detection profile includes a refractory period and a sensing period, the refractory period being applied to a first portion of the cardiac cycle and the sensing period being applied to at least a second portion of the cardiac cycle; and the operational circuitry is configured to calculate a measure of biphasic or monophasic nature of cardiac cycles by comparing an average sensed positive amplitude from the first portion of several of the cardiac cycles to an average sensed negative amplitude from the first portion of several of the cardiac cycles.

An eighteenth illustrative example builds on the thirteenth illustrative example, wherein the operational circuitry is configured to combine the signal to noise ratio, cardiac signal amplitude and measure of biphasic or monophasic nature of cardiac signals to generate a sensing quality metric for the first sensing vector comprises the operational circuitry by finding the sum or product of: a first metric related to the signal to noise ratio; a second metric related to the cardiac signal amplitude; and a third metric related to the measure of biphasic or monophasic nature of cardiac signals.

A nineteenth illustrative example builds on the thirteenth illustrative example, wherein the operational circuitry is configured to combine the signal to noise ratio, cardiac signal amplitude and measure of biphasic or monophasic nature of cardiac signals to generate a sensing quality metric for the first sensing vector comprises the operational circuitry by calculating a sensing vector score for the first vector using the signal to noise ratio and the cardiac signal amplitude, and adjusting the score in view of the measure of biphasic or monophasic nature of cardiac signals.

A twentieth illustrative example builds on the thirteenth illustrative example, wherein the operational circuitry is further configured to perform the following: for a second sensing vector, the operational circuitry calculating each of: an estimate of signal-to-noise ratio; an estimate of cardiac signal amplitude; and a measure of biphasic or monophasic nature of sensed signals; and combining the signal to noise ratio, cardiac signal amplitude and measure of biphasic or monophasic nature of sensed signals to generate a sensing quality metric for the second sensing vector; and using the sensing quality metrics for the first and second sensing vectors to select from at least the first and second sensing vectors a sensing vector for use in cardiac signal analysis.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An implantable cardiac device comprising:
a plurality of electrodes configured for sensing electrical signals; and
operational circuitry configured for analyzing signals received from the sensing electrodes,
wherein the operational circuitry and electrodes are configured to define at least two sensing vectors for sensing cardiac signals and the operational circuitry is configured to perform the following:
for a first sensing vector, calculating each of:
an estimate of signal-to-noise ratio;
an estimate of cardiac signal amplitude; and
a measure of biphasic or monophasic nature of sensed signals; and
combining the signal to noise ratio, cardiac signal amplitude and measure of biphasic or monophasic nature of sensed signals to generate a sensing quality metric for the first sensing vector;
wherein:
the operational circuitry is further configured to sense a plurality of cardiac cycles with selected electrodes for the first vector by applying a detection profile to a sensed cardiac signal to detect a cardiac cycle, wherein the detection profile includes a refractory period and a sensing period, the refractory period being applied to a first portion of the cardiac cycle and the sensing period being applied to at least a second portion of the cardiac cycle; and
the operational circuitry is configured to calculate a measure of biphasic or monophasic nature of cardiac cycles by comparing an average sensed positive amplitude from the first portion of two or more of the cardiac cycles to an average sensed negative amplitude from the first portion of two or more of the cardiac cycles.

2. An implantable cardiac device comprising:
a plurality of electrodes configured for sensing electrical signals; and
operational circuitry configured for analyzing signals received from the sensing electrodes,
wherein the operational circuitry and electrodes are configured to define at least two sensing vectors for sensing cardiac signals and the operational circuitry is configured to perform the following:
for a first sensing vector, calculating each of:
an estimate of signal-to-noise ratio;
an estimate of cardiac signal amplitude; and
a measure of biphasic or monophasic nature of sensed signals; and
combining the signal to noise ratio, cardiac signal amplitude and measure of biphasic or monophasic nature of sensed signals to generate a sensing quality metric for the first sensing vector;
wherein:
the operational circuitry is configured to combine the signal to noise ratio, cardiac signal amplitude and measure of biphasic or monophasic nature of cardiac signals to generate a sensing quality metric for the first sensing vector comprises the operational circuitry by finding the sum or product of:
a first metric related to the signal to noise ratio;
a second metric related to the cardiac signal amplitude; and
a third metric related to the measure of biphasic or monophasic nature of cardiac signals.

3. An implantable cardiac device comprising:
a plurality of electrodes configured for sensing electrical signals while implanted; and
operational circuitry configured for analyzing signals received from the sensing electrodes,
wherein the operational circuitry and electrodes are configured to define at least two sensing vectors for sensing cardiac signals and the operational circuitry is configured to perform the following:
for a first sensing vector, calculating each of:
an estimate of signal-to-noise ratio;
an estimate of cardiac signal amplitude; and
a measure of biphasic or monophasic nature of sensed signals; and
combining the signal to noise ratio, cardiac signal amplitude and measure of biphasic or monophasic nature of sensed signals to generate a sensing quality metric for the first sensing vector;
wherein:
the operational circuitry is configured to combine the signal to noise ratio, cardiac signal amplitude and measure of biphasic or monophasic nature of cardiac signals to generate a sensing quality metric for the first sensing vector comprises the operational circuitry by calculating a sensing vector score for the first vector using the signal to noise ratio and the cardiac signal amplitude, and adjusting the score in view of the measure of biphasic or monophasic nature of cardiac signals.

4. The implantable cardiac device of claim 1 wherein the operational circuitry is further configured to perform the following:
for a second sensing vector, the operational circuitry calculating each of:
an estimate of signal-to-noise ratio;
an estimate of cardiac signal amplitude; and
a measure of biphasic or monophasic nature of sensed signals; and
combining the signal to noise ratio, cardiac signal amplitude and measure of biphasic or monophasic nature of sensed signals to generate a sensing quality metric for the second sensing vector; and
using the sensing quality metrics for the first and second sensing vectors to select from at least the first and second sensing vectors a sensing vector for use in cardiac signal analysis.

5. The implantable cardiac device of claim 1 wherein the operational circuitry is further configured to select a default sensing vector for use in the analysis of cardiac signals using at least one factor related to the measure of biphasic or monophasic nature of cardiac signals generated for the first sensing vector.

6. The implantable cardiac device of claim 1, wherein, in order to establish a measure of biphasic or monophasic nature of cardiac signals, the operational circuitry performs the following:
   identifying a QRS portion of a cardiac cycle; and
   comparing a positive peak in the QRS portion of the cardiac cycle to a negative peak in the QRS portion of the cardiac cycle.

7. The implantable cardiac device of claim 1 wherein, in order to establish a measure of biphasic or monophasic nature of cardiac signals, the operational circuitry performs the following:
   detecting an event in a signal sensed along the first sensing vector;
   defining a window associated with the detected event; and
   comparing a positive peak in the window to a negative peak in the window.

8. The implantable cardiac device of claim 1 wherein the operational circuitry is further configured to calculate the estimate of cardiac signal amplitude by analyzing a sensed amplitude from the first portion of the cardiac cycle for each of two or more cardiac cycles.

9. The implantable cardiac device of claim 1 wherein the operational circuitry is further configured to calculate an estimate of signal to noise ratio by comparing a sensed amplitude from the first portion of the cardiac cycle to a sensed amplitude from the second portion of the cardiac cycle for each of two or more cardiac cycles.

10. The implantable cardiac device of claim 2 wherein the operational circuitry is further configured to perform the following:
    for a second sensing vector, the operational circuitry calculating each of:
      an estimate of signal-to-noise ratio;
      an estimate of cardiac signal amplitude; and
      a measure of biphasic or monophasic nature of sensed signals; and
    combining the signal to noise ratio, cardiac signal amplitude and measure of biphasic or monophasic nature of sensed signals to generate a sensing quality metric for the second sensing vector; and
    using the sensing quality metrics for the first and second sensing vectors to select from at least the first and second sensing vectors a sensing vector for use in cardiac signal analysis.

11. The implantable cardiac device of claim 2 wherein the operational circuitry is further configured to select a default sensing vector for use in the analysis of cardiac signals using at least one factor related to the measure of biphasic or monophasic nature of cardiac signals generated for the first sensing vector.

12. The implantable cardiac device of claim 2, wherein, in order to establish a measure of biphasic or monophasic nature of cardiac signals, the operational circuitry performs the following:
    identifying a QRS portion of a cardiac cycle; and
    comparing a positive peak in the QRS portion of the cardiac cycle to a negative peak in the QRS portion of the cardiac cycle.

13. The implantable cardiac device of claim 2 wherein, in order to establish a measure of biphasic or monophasic nature of cardiac signals, the operational circuitry performs the following:
    detecting an event in a signal sensed along the first sensing vector;
    defining a window associated with the detected event; and
    comparing a positive peak in the window to a negative peak in the window.

14. The implantable cardiac device of claim 2 wherein the operational circuitry is further configured to calculate a measure of biphasic or monophasic nature of cardiac cycles by comparing a sensed positive amplitude from the first portion of the cardiac cycle to a sensed negative amplitude from the first portion of the cardiac cycle for each of two or more cardiac cycles.

15. The implantable cardiac device of claim 3 wherein the operational circuitry is further configured to perform the following:
    for a second sensing vector, the operational circuitry calculating each of:
      an estimate of signal-to-noise ratio;
      an estimate of cardiac signal amplitude; and
      a measure of biphasic or monophasic nature of sensed signals; and
    combining the signal to noise ratio, cardiac signal amplitude and measure of biphasic or monophasic nature of sensed signals to generate a sensing quality metric for the second sensing vector; and
    using the sensing quality metrics for the first and second sensing vectors to select from at least the first and second sensing vectors a sensing vector for use in cardiac signal analysis.

16. The implantable cardiac device of claim 3 wherein the operational circuitry is further configured to select a default sensing vector for use in the analysis of cardiac signals using at least one factor related to the measure of biphasic or monophasic nature of cardiac signals generated for the first sensing vector.

17. The implantable cardiac device of claim 2, wherein, in order to establish a measure of biphasic or monophasic nature of cardiac signals, the operational circuitry performs the following:
    identifying a QRS portion of a cardiac cycle; and
    comparing a positive peak in the QRS portion of the cardiac cycle to a negative peak in the QRS portion of the cardiac cycle.

18. The implantable cardiac device of claim 2 wherein, in order to establish a measure of biphasic or monophasic nature of cardiac signals, the operational circuitry performs the following:
    detecting an event in a signal sensed along the first sensing vector;
    defining a window associated with the detected event; and
    comparing a positive peak in the window to a negative peak in the window.

19. The implantable cardiac device of claim 2 wherein the operational circuitry is further configured to calculate a measure of biphasic or monophasic nature of cardiac cycles by comparing a sensed positive amplitude from the first portion of the cardiac cycle to a sensed negative amplitude from the first portion of the cardiac cycle for each of two or more cardiac cycles.

\* \* \* \* \*